United States Patent [19]

Hagiwara et al.

[11] Patent Number: 5,419,333
[45] Date of Patent: May 30, 1995

[54] ULTRASONIC DOPPLER BLOOD FLOW METER APPARATUS

[75] Inventors: Hisashi Hagiwara, Yokohama; Hiroshi Fukukita, Tokyo; Morio Nishigaki, Fujisawa; Yoshihiko Ito, Yokohama, all of Japan

[73] Assignee: Matsushita Electric Industrial Co., Ltd., Osaka, Japan

[21] Appl. No.: 202,471

[22] Filed: Feb. 28, 1994

[30] Foreign Application Priority Data

Jun. 8, 1993 [JP] Japan .................................. 5-137285

[51] Int. Cl.⁶ .............................................. A61B 8/00
[52] U.S. Cl. .............................................. 128/661.09
[58] Field of Search ...................... 128/661.08, 661.09, 128/661.1, 662.01, 662.02, 660.05; 73/861.25

[56] References Cited

U.S. PATENT DOCUMENTS 5,152,292 10/1992 Karp ................................ 128/661.09
5,163,434 11/1992 Kumazawa ...................... 128/661.09
5,211,169 5/1993 Freeland .......................... 128/661.1

FOREIGN PATENT DOCUMENTS 63-84532 4/1988 Japan .

Primary Examiner—George Manuel
Attorney, Agent, or Firm—Stevens, Davis, Miller & Mosher

[57] ABSTRACT

An ultrasonic Doppler blood flow meter apparatus includes a wall filter for eliminating clutter from an echo signal of an ultrasonic pulse signal sent to a living being under test. The wall filter includes a switch for cutting a part of input data and a control unit for controlling the switch such that the switch is opened during a period in which first m data (where m is integer) is inputted to undergo filtering by the wall filter while the switch is closed during a period in which data following the (m+1)-th data inclusive thereof are inputted.

6 Claims, 5 Drawing Sheets

ULTRASONIC DOPPLER BLOOD FLOW METER APPARATUS

BACKGROUND OF THE INVENTION

The present invention relates to an ultrasonic Doppler blood flow meter apparatus for measuring blood flow in living beings by utilizing an ultrasonic Doppler method in the medical field for thereby generating blood flow images.

There is known a two-dimensional ultrasonic Doppler blood flow meter apparatus in whcih a blood flow distribution in a living being is determined by making use of an ultrasonic Doppler's effect and displayed in superposition on a two-dimensional monochromatic tomograph with the blood flow distribution being displayed is a color. This apparatus is also known as a color flow apparatus. The structure of the two-dimensional Doppler blood flow meter apparatus known heretofore is shown in FIG. 7.

Referring to FIG. 7, an ultrasonic transmitter 1 emits ultrasonic pulses through the medium of a probe 2 for irradiation of a portion of a living being. Echoes generated as the result of the irradiation with the ultrasonic pulses are converted into an electric signal through the probe 2, which signal is then amplified by a receiver 3 and undergoes phase shift detection by a phase shift detector 4 to be thereby converted to a Doppler shift signal. The Doppler shift signal outputted from the phase shift detector 4 is converted into digital data through an analogue-to-digital (A/D) converter 5, the digital data then being inputted to a wall filter 6 which is generally constituted by a FIR- or IIR-type filter of degree several and which serves to eliminate unwanted signal components of low frequencies (usually referred to as the clutter) which originate in intravital tissues. FIG. 6 shows, by way of example, a major portion of the wall filter constituted by an IIR-type filter of second degree or order. The wall filter 6 of this configuration is featured in that the characteristic equivalent to that of the FIR-type filter can be realized by using a smaller number of multipliers and adders when compared with the FIR-type filter and that the cut-off characteristic can flexibly be modified by changing the feedback coefficients K1 and K2. The Doppler shift signal from which the clutter signals are eliminated by the wall filter 6 is supplied to a blood flow rate arithmetic unit 7 which is adapted to determine arithmetically the blood flow rates. The output of the blood flow rate arithmetic unit 7 is then inputted to a digital scan converter (hereinafter referred to as the DSC in abbreviation) 9 together with a B-mode signal outputted from an envelope detector 8. In the DSC 9, the B-mode signal and the blood flow rate signal are mixed together, whereby a two-dimensional blood flow image is displayed on a screen of a monitor display unit 10.

In the ultrasonic Doppler blood flow meter apparatus known heretofore, it is desirable to impart steep characteristics to the wall filter 6 in order to provide highly accurate blood flow information. In that case, however, remarkably large transient responses tend to take place, making it difficult or impossible to obtain the blood information with high accuracy because the data contains the transient responses. Under the circumstances, when the blood flow rate is to be arithmetically determined with reasonable accuracy, much of the data will have to be discarded, resulting in that the amount of data supplied to the blood flow rate arithmetic unit will significantly be decreased, resulting in a problem that S/N ratio is degraded because the number of samplings decreases. On the other hand, when the number of data samplings is increased in order to compensate for the data lost, it is then required to increase the number of times the ultrasonic pulse is sent out and the echo is received in the same direction, which will however result in degradation in the frame rate.

SUMMARY OF THE INVENTION

In the light of the state of the art described above, it is an object of the present invention to solve the problems of the blood flow meter apparatus known heretofore and provide an improved two-dimensional ultrasonic Doppler blood flow meter apparatus which can ensure availability of the blood flow information with enhanced accuracy.

For achieving the object described above, there is provided, according to an aspect of the invention, an ultrasonic Doppler blood flow meter apparatus which comprises a wall filter for eliminating clutters from an echo signal of an ultrasonic pulse signal sent to a living being under test, the wall filter having a switch for cutting a part of the input data, and a control unit for controlling the switch such that the switch is opened during a period in which first m data (where m is integer) is inputted to undergo filtering by the wall filter while the switch is closed during a period in which data following the (m+1)-th data inclusive thereof are inputted.

In the ultrasonic Doppler blood flow meter apparatus described above, the switch control unit opens the switch during a period in which one or more data sets containing the influential transient response is being inputted for the filtering operation, to thereby prevent the data having influential transient response from being transmitted to the filter block provided downstream of the switch. Thus, the transient response of the wall filter can be reduced with simple hardware configuration while ensuring availability of blood flow information with high accuracy.

DESCRIPTION OF THE PREFERRED EMBODIMENTS

Figure 1:
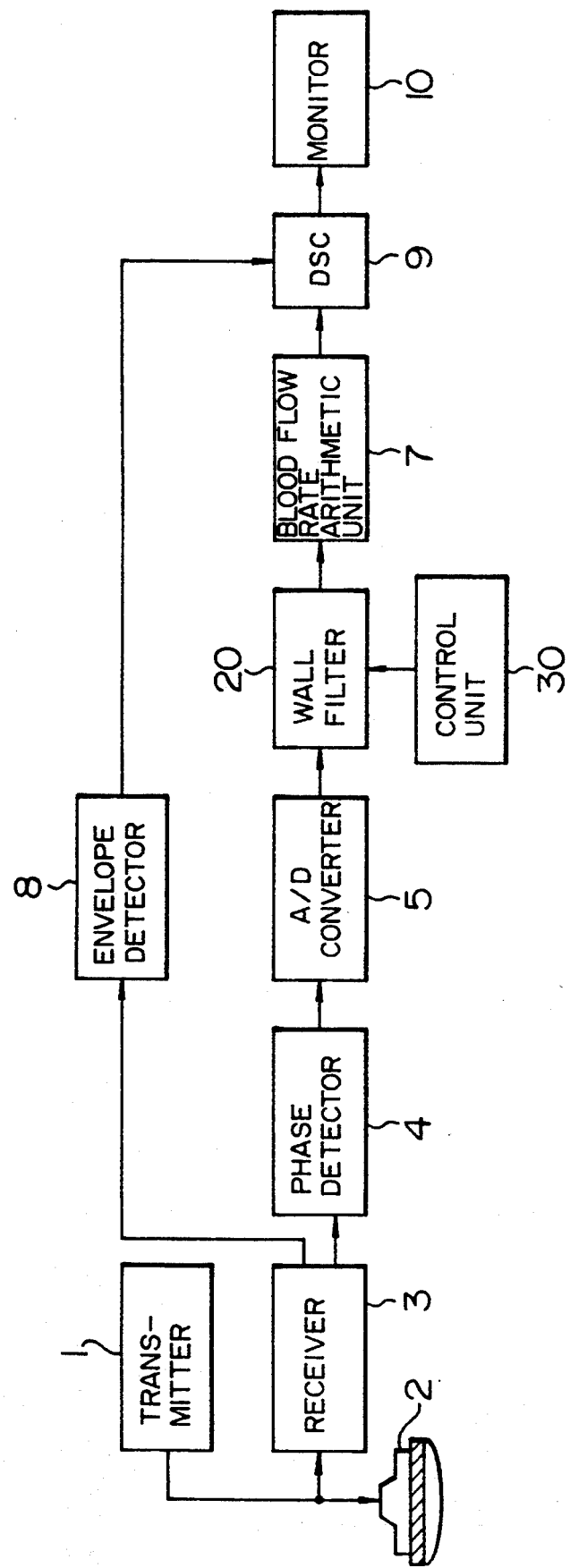
FIG. 1 is a schematic block diagram showing generally a structure of an ultrasonic Doppler blood flow meter apparatus according to a first embodiment of the invention.

FIG. 1 shows the structure of an ultrasonic Doppler blood flow meter apparatus according to a first embodiment of the invention. In the figure, the transmitter 1, the probe 2, the receiver 3, the phase shift detector 4, the A/D converter 5, the blood flow rate arithmetic unit 7, the envelope detector 8, the DSC 9 and the monitor 10 are the same as or equivalent to those described hereinbefore in conjunction with the blood flow meter apparatus known heretofore in respect to the structure as well as operation. Accordingly, repeated description thereof is unnecessary.

Figure 2:
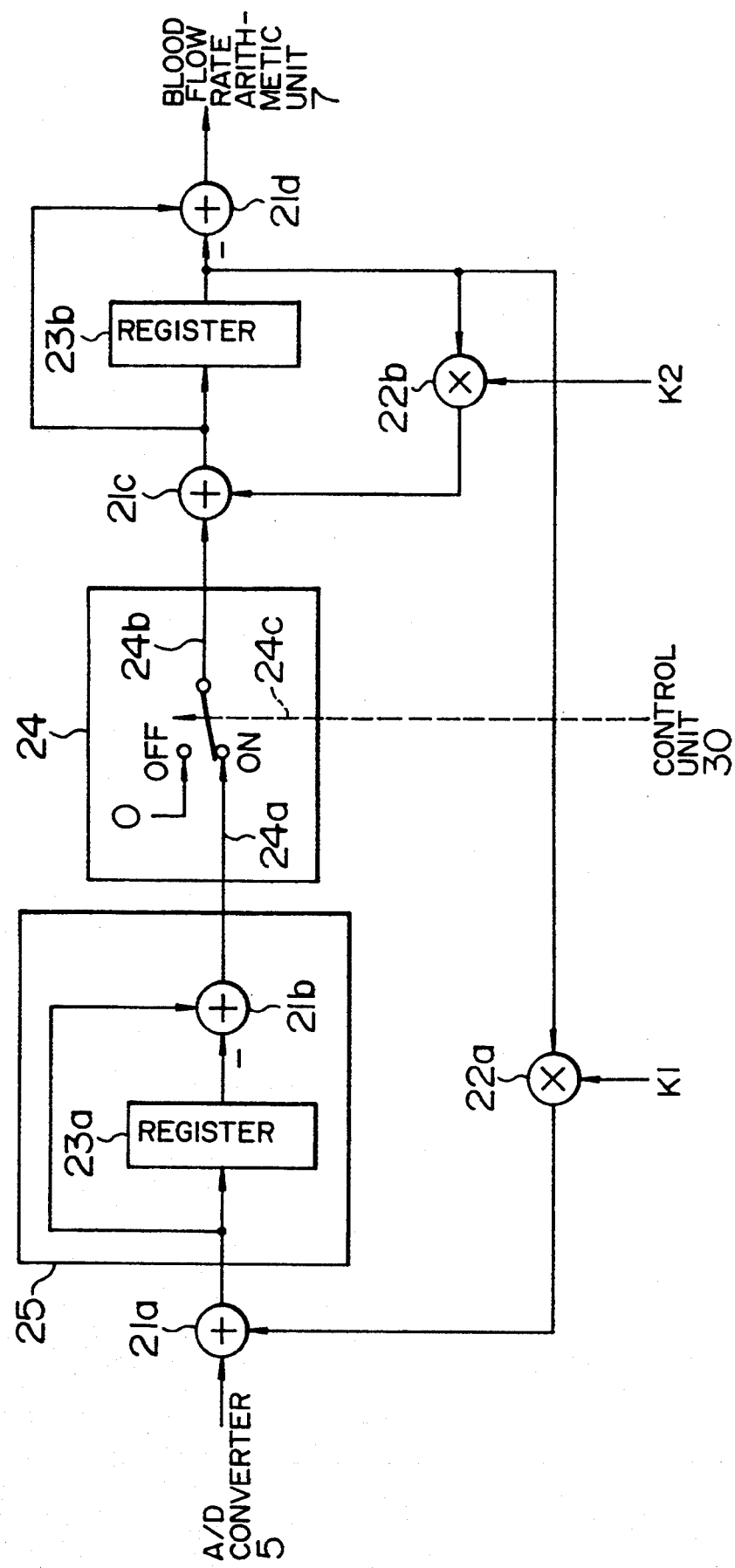
FIG. 2 is a block diagram showing in detail the structure of a wall filter employed in the apparatus shown in FIG. 1.

According to the invention, there is provided a wall filter 20 including a switch 24 and a control unit 30 for controlling the switch. FIG. 2 is a block diagram showing in detail the structure of a wall filter employed in the apparatus shown in FIG. 1. As can be seen in this figure, the wall filter 20 includes a switch 24 controlled by the control unit 30. Now, referring to the input side of the switch 24 extending from the A/D converter 5 as the preceding stage while the output side of the switch 24 leading to the blood flow rate arithmetic unit 7 is referred to as the succeeding stage; there is implemented in the preceding stage a filter 25 by a register 23a and an adder 21b, which filter 25 has a characteristic of $(1-Z^{-1})$ representing Z-transformation. This filter 25 is an FIR-type filter of first degree (or order) and exhibits such characteristic that only the first data of an input data train or sequence contains transient response with the following data, inclusive of the second, having no transient response. The output of the filter 25 (i.e., output of the adder 21b) of the preceding stage is connected to the input of the succeeding stage (i.e., input of the adder 21c) by way of the switch 24 provided according to the teachings of the invention.

In the ON-state of the switch 24, an input line 24a is connected to an output line 24b. On the other hand, when the switch 24 is opened (OFF-state), a constant of zero is connected to the output line 24b. The "ON" and "OFF" states of the switch 24 are controlled by the control unit 30 via a control line 24c.

Figure 3:
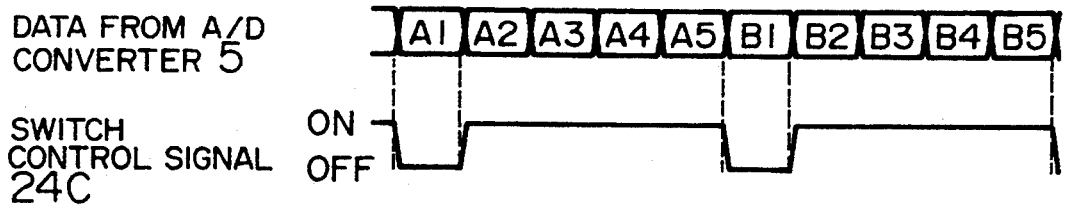
FIG. 3 is a timing chart for illustrating operation of a control unit of the blood flow meter apparatus according to the first embodiment of the invention.

FIG. 3 shows, by way of example, the timing at which the control signal is generated by the control unit 30. In the case of this example, it is assumed that the transmission/reception of the ultrasonic pulse signal in the same direction is repeated five times. The data A1 to A5 and B1 to B5 outputted from the A/D converter 5 represent trains or sequences of Doppler shift signal data obtained from a same location of a living being under test. When the first data (A1 and B1) of each data sequence is inputted to the filter, the switch 24 is opened (i.e., set to the OFF-state). On the other hand, upon inputting of second to fifth data (A2-A5 and B2-B5), the switch 24 is closed (ON-state).

In this manner, in the filter circuit of the succeeding stage disposed downstream of the switch 24, zero is inputted instead of data containing the transient response due to filtering through the preceding filter stage 25, when the first data is inputted, while for the succeeding data inclusive of the second data, data containing no influence of the transient response due to filtering through the preceding stage filter 25 are inputted.

As is apparent from the above, through operation of the control unit 30 and the switch 24, the data exhibiting no transient response is transmitted from the filter 25 of the preceding stage to the filter of the succeeding stage, as a result of which the influence of a transient response contained in the data sent to the blood flow rate arithmetic unit 7 can be suppressed to a minimum.

Figure 4:
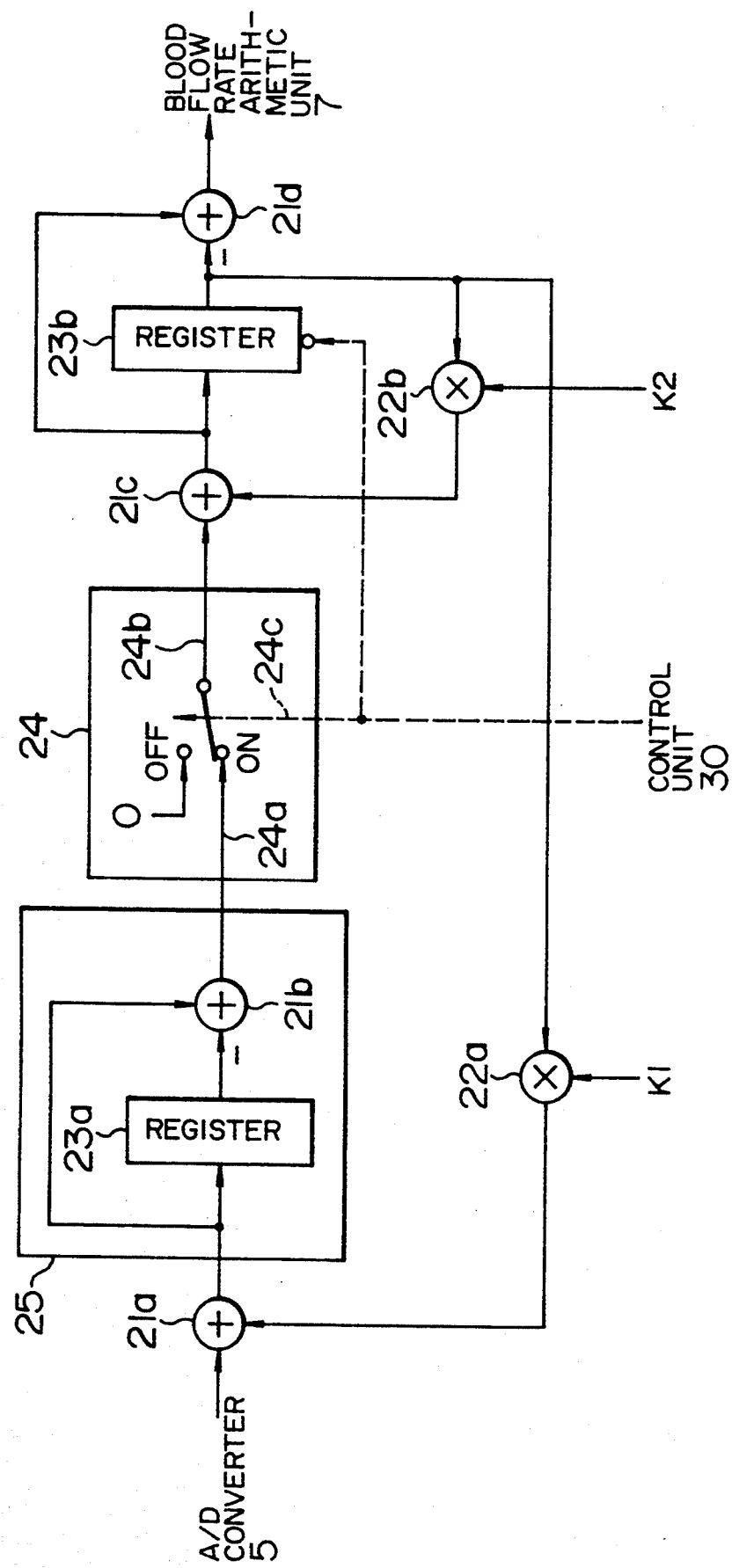
FIG. 4 is a block diagram showing in detail the structure of the wall filter according to a second embodiment of the invention.
Figure 7:
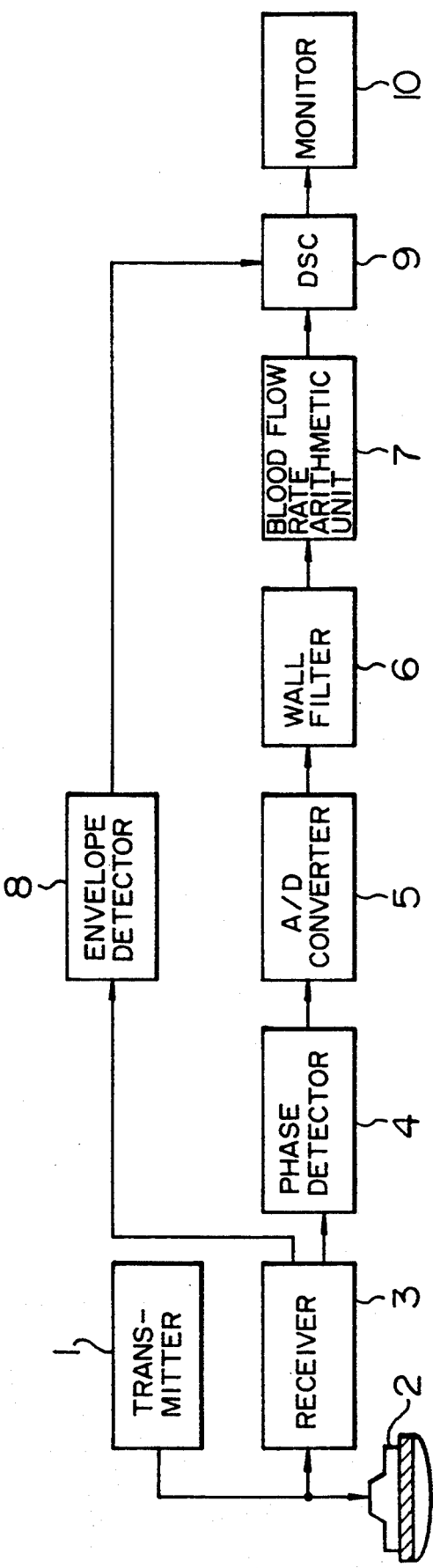
FIG. 7 is a block diagram showing the structure of a conventional blood flow meter apparatus.

FIG. 4 is a block diagram showing in detail the structure of the wall filter according to a second embodiment of the invention. The wall filter according to the instant embodiment differs from that of the first embodiment in that the register 23b shown in FIG. 4 is provided with a zero-clear terminal, whereby the contents of the register 23b is cleared to zero at the timing when the switch 24 is opened.

Figure 5:
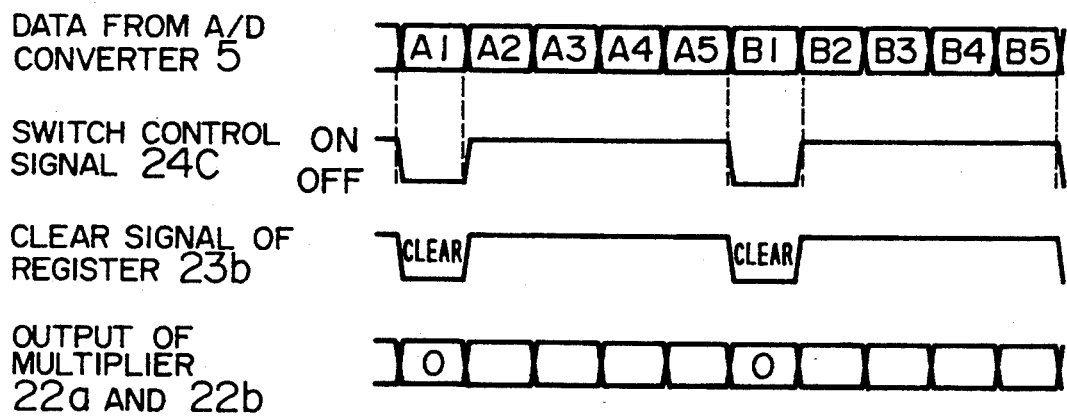
FIG. 5 is a timing chart for illustrating operation of a control unit in the apparatus according to the second embodiment of the invention.
Figure 6:
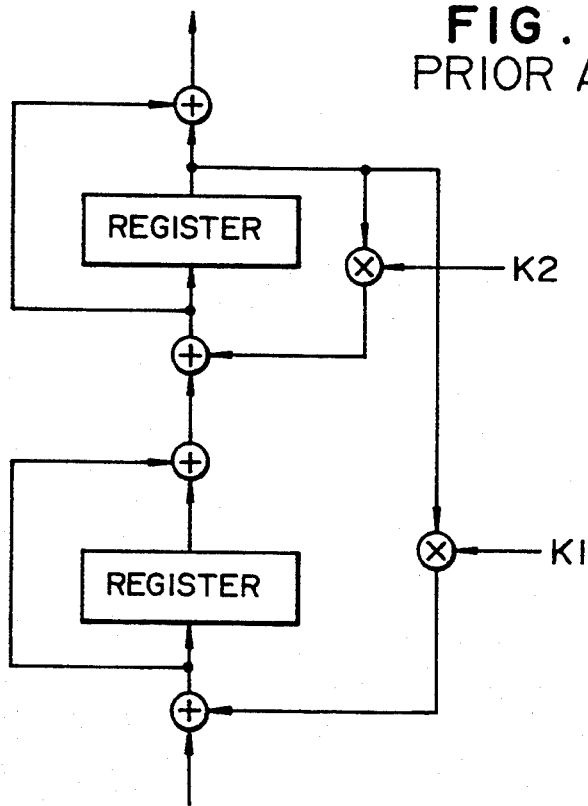
FIG. 6 is a block diagram showing the structure of the wall filter of an ultrasonic Doppler blood flow meter apparatus hitherto known.

FIG. 5 is a timing chart for illustrating operation of the control unit 30 in the apparatus according to the second embodiment of the invention. As can be seen in the figure, the content of the register 23b is cleared to zero at the time point when the first data of each data sequence is inputted to the filter, whereby the outputs of multipliers 22a and 22b are reset to zero. Thus, influence of the preceding data sequence is prevented from being fed back.

In this manner, according to the teachings of the invention incarnated in the second embodiment, the transient response of the filter can further be reduced by virtue of such arrangement that the content of the register of the succeeding stage is cleared to zero every time the first data of the data sequence is inputted in addition to suppression of the transient response of the filter of the preceding stage by means of the control unit 30 and the switch 22.

In conjunction with the first and second embodiments, it has been described that the FIR-type filter of first degree is used as the filter 25 of the preceding stage with the IIR-type filter being used in the succeeding stage for implementing the wall filter 20. It should however be understood the filter of IIR type or FIR type may be used in both of the preceding and succeeding stages, substantially to the same effects.

It should further be mentioned that filters of several degrees may be used as the filters of the preceding and succeeding stages. In that case, the switch 24 is opened during a period in which the first m data (m is an integer) to be filtered through the wall filter is inputted, wherein the number m is determined in the manner, as mentioned below. When the FIR-type filters are disposed in series in the preceding stage in a number n (n is an integer) at maximum, the number of the registers in the preceding stage is n at maximum in the serial direction. In this case, the data up to the n-th data in the output data sequence contain the transient response. Thus, by determining the value of m so that m=n, it is possible to reduce the influence of transient response contained in the data sent to the blood flow rate arithmetic unit 7 to a negligible level. When the preceding stage is constituted by the IIR-type filter, the transient response in the preceding stage can not completely be nullified. However, influence of the transient response can previously be estimated by computation or simulation. Accordingly, the value of m for which the switch 24 is opened can be selected such that the transient response occurring in the preceding stage can sufficiently be eliminated while an amount of data to be discarded can be minimized. The value of m thus determined can previously be set at the control unit 30. Besides, the value now of concern can be changed by issuing corresponding commands to the control unit while observing the picture generated actually in the course of operation of the ultrasonic Doppler blood flow meter apparatus.

Although it has been described in conjunction with the first and second embodiments of the invention that the switch 24 is provided internally of the wall filter 20, it is of course possible to provide it externally of the wall filter 20. Besides, it is of no matter whether or not the switch 24 is implemented integrally with the wall filer 20. What is required is that a filter including the register is disposed at the side upstream of the switch 24.

As is apparent from the foregoing description, according to the teachings of the invention, such control can be realized that transient response generated by the filter of the preceding stage is essentially prevented from being transmitted to the filter of the succeeding stage, whereby the transient response of the wall filter can be suppressed to a very low level with the addition of a small amount of hardware, to a great advantage. Thus, even in the case where steep filter characteristic is set for the wall filter, the blood flow rate can accurately be estimated with improved S/N ratio at a high frame rate because the data to be discarded can be suppressed to a maximum.

We claim:

1. An ultrasonic Doppler blood flow meter apparatus, comprising:

a wall filter for eliminating clutter from an echo signal of an ultrasonic pulse signal sent to a living being under test;

said wall filter having a switch for removing a part of input data; and control means for controlling opening and closing of said switch such that said switch is opened during a period in which first m data (where m is integer) are inputted to undergo filtering by said wall filter, and said switch is closed during a period in which data following the (m+1)-th data, inclusive thereof, are inputted to undergo filtering by said wall filter.

2. An ultrasonic Doppler blood flow meter apparatus according to claim 1, wherein said wall filter further includes a first filter provided at the data input side and having a characteristic given by the Z-transformation $(1-Z^{-1})$ and a second filter provided at the data output side, said first filter being connected to said second filter by way of said switch, and wherein said control means controls said switch such that said switch is opened during a period in which initial data of an input data train originating for a particular location of the living being under test are inputted to said first filter while said switch is closed during a period in which data following the initial data are inputted to said first filter.

3. An ultrasonic Doppler blood flow meter apparatus according to claim 1, wherein said wall filter further comprises a filter, operatively associated with an output of said switch, comprising a data register for eliminating unwanted signal components of low frequencies, said data register being cleared to zero in response to said switch being opened.

4. A filtering system for an ultrasonic Doppler blood flow meter apparatus, said filtering apparatus comprising:

a wall filter for eliminating clutter from an echo signal of an ultrasonic pulse signal sent to a living being under test;

said wall filter having a switch for removing a part of input data; and control means for controlling opening and closing of said switch such that said switch is opened during a period in which first m data (where m is integer) are inputted to undergo filtering by said wall filter, and said switch is closed during a period in which data following the (m+1)-th data, inclusive thereof, are inputted to undergo filtering by said wall filter.

5. A filtering apparatus according to claim 4, wherein said wall filter further includes a first filter provided at the data input side and having a characteristic given by the Z-transformation $(1-Z^{-1})$ and a second filter provided at the data output side, said first filter being connected to said second filter by way of said switch, and wherein said control means controls said switch such that said switch is opened during a period in which initial data of an input data train originating for a particular location of the living being under test are inputted to said first filter while said switch is closed during a period in which data following the initial data are inputted to said first filter.

6. A filtering apparatus according to claim 4, wherein said wall filter further comprises a filter, operatively associated with an output of said switch, comprising a data register for eliminating unwanted signal components of low frequencies, said data register being cleared to zero in response to said switch being opened.

* * * * *